(12) United States Patent
Bouton

(10) Patent No.: US 8,708,908 B2
(45) Date of Patent: Apr. 29, 2014

(54) ACCESS DISCONNECT DETECTION SYSTEM

(75) Inventor: Chad E. Bouton, Powell, OH (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

(21) Appl. No.: 13/527,170

(22) Filed: Jun. 19, 2012

(65) Prior Publication Data
US 2012/0259284 A1 Oct. 11, 2012

Related U.S. Application Data

(63) Continuation of application No. 11/859,589, filed on Sep. 21, 2007, now Pat. No. 8,221,320.

(51) Int. Cl.
*A61B 5/00* (2006.01)
*A61M 37/00* (2006.01)

(52) U.S. Cl.
USPC .......................................... 600/371; 604/4.01

(58) Field of Classification Search
CPC ........... A61B 5/02042; A61M 1/3653; A61M 2001/3656
USPC .................. 600/371; 604/4.01–6.16
See application file for complete search history.

(56) References Cited

U.S. PATENT DOCUMENTS

| | | | |
|---|---|---|---|
| 4,510,489 A | 4/1985 | Anderson, III et al. | |
| 5,261,874 A | 11/1993 | Castle | |
| 5,427,695 A | 6/1995 | Brown | |
| 5,973,598 A * | 10/1999 | Beigel | 340/572.1 |
| 6,069,564 A | 5/2000 | Hatano et al. | |
| 6,071,421 A | 6/2000 | Brown | |
| 6,154,137 A | 11/2000 | Goff et al. | |
| 6,509,217 B1 | 1/2003 | Reddy | |
| 6,897,809 B2 | 5/2005 | Carson et al. | |

(Continued)

FOREIGN PATENT DOCUMENTS

| | | |
|---|---|---|
| GB | 2179738 A | 3/1987 |
| WO | 99/17692 | 4/1999 |
| WO | 2007/121398 A2 | 10/2007 |

OTHER PUBLICATIONS

Vincent et al. Presence of Blood Significant Decreases Transmission of 630 nm Laser Light. Lasers in Surgery and Medicine 11:399-403 (1991).*

(Continued)

*Primary Examiner* — Patricia Mallari
*Assistant Examiner* — Christian Jang
(74) *Attorney, Agent, or Firm* — K&L Gates LLP

(57) ABSTRACT

An access site disconnection system and method are disclosed. Radio frequency transmitters and receivers are placed near an access site. When a patient receives dialysis treatment, wetness may arise from blood if the access needle becomes disconnected from the access site. Radio-frequency transmitters are mounted on or near gauze or other absorbent material placed adjacent the access site, as are radio-frequency receivers. After the sensors are placed, the dialysis machine and radio-frequency control circuit may be initialized or baselined, and dialysis treatment, such as hemodialysis, begun. If blood leaks from the access site, such as if the access needle is dislodged, the blood attenuates the radio frequency transmissions, which are detected by the receivers. A signal is sent to a controller or to an output device to raise an alert or sound an alarm.

20 Claims, 7 Drawing Sheets

(56) References Cited

U.S. PATENT DOCUMENTS

| | | |
|---|---|---|
| 7,050,047 B2 | 5/2006 | Hong |
| 7,052,480 B2 | 5/2006 | Han et al. |
| 7,059,518 B2 | 6/2006 | Forster |
| 7,102,572 B2 | 9/2006 | Okado |
| 7,170,414 B2 | 1/2007 | Clifford et al. |
| 2002/0198483 A1 | 12/2002 | Wariar et al. |
| 2003/0009123 A1 | 1/2003 | Brugger et al. |
| 2004/0212504 A1 | 10/2004 | Forcier et al. |
| 2005/0038325 A1* | 2/2005 | Moll ............................. 600/300 |
| 2005/0064825 A1* | 3/2005 | Forrester ...................... 455/101 |
| 2006/0097920 A1 | 5/2006 | Lin et al. |
| 2006/0130591 A1 | 6/2006 | Perkins |
| 2007/0096919 A1 | 5/2007 | Knadle, Jr. et al. |
| 2008/0065006 A1 | 3/2008 | Roger |
| 2008/0195021 A1 | 8/2008 | Roger |
| 2008/0195060 A1 | 8/2008 | Roger |
| 2009/0079578 A1 | 3/2009 | Dvorsky |
| 2009/0080757 A1 | 3/2009 | Roger |
| 2009/0082647 A1 | 3/2009 | Busby |
| 2009/0082649 A1 | 3/2009 | Muller |
| 2009/0082653 A1 | 3/2009 | Rohde |
| 2009/0082676 A1 | 3/2009 | Bennison |
| 2009/0088612 A1 | 4/2009 | Bouton |
| 2009/0088613 A1 | 4/2009 | Marttila |
| 2009/0088683 A1 | 4/2009 | Roger |
| 2009/0105627 A1 | 4/2009 | Rohde |
| 2010/0022934 A1 | 1/2010 | Hogard |
| 2010/0022935 A1 | 1/2010 | Muller |

OTHER PUBLICATIONS

European Office Action issued Feb. 12, 2013 for related European Appln. No. 08770292.4.

* cited by examiner

ACCESS DISCONNECT DETECTION SYSTEM

PRIORITY

This application claims priority to and the benefit as a continuation application of U.S. patent application entitled "Access Disconnect Detection System", Ser. No. 11/859,589, filed Sep. 21, 2007, the entire contents of which are incorporated herein by reference and relied upon.

The field of the invention is medical treatments generally and patient vascular access systems. The present invention relates to embodiments of a method and a system for detecting disconnection of an access needle or catheter while receiving medical treatment.

The maxim of "first, do no harm," may be a good summary of the Hippocratic oath required of doctors and practiced by medical professionals. Nowhere is this principle required more than in modern medicine. With patients living longer, there are more extended treatments and more frail patients than ever. Such patients are in danger from a number of complications that can arise from continuing therapeutic procedures, and even from diagnostic procedures, that are necessary for their continued care. Treatments involving extracorporeal blood treatment are clear examples.

The most obvious danger is infection, but the harm caused by infection can be overcome by not re-using even supposedly-sterile devices, by diligent attention by the patient himself or herself, and by the careful attention of care givers attending the patient. Other problems also arise, but, like infections, have been difficult to eradicate. One of the problems arises in blood treatment procedures in which the patient's blood is physically removed for treatment and then returned, all in the same procedure. Removal and return of blood is practiced in hemodialysis, for those persons whose kidneys do not function well. Other procedures, such as apheresis, involve removing blood from a patient or a donor, subjecting the blood to a centrifugal treatment to separate blood platelets or plasma from red blood cells, and then returning the red blood cells to the patient or donor, as described in U.S. Pat. Nos. 5,427,695 and 6,071,421.

The extracorporeal medical treatments described above require that the blood be removed for treatment and then returned. This requires access to the patient's vascular system, from which blood is removed and to which blood is then returned. If a "batch" treatment is used, that is, a quantity of blood is withdrawn, treated and returned, only a single needle is used. Each batch treatment is typically short, and the treatment is attended by a medical professional at a clinic or hospital. Other treatments are continuous, such as the platelet separation discussed above, or dialysis treatment, and may require a duration of several hours or even overnight. There is also a "batch continuous" method in which a single needle is used. There are distinct draw and return phases of a batch continuous process. During the draw phase, blood is processed and additional blood is sent to a holding container to the processed during the return phase. During the return phase, blood is processed from the holding container and returned to the patient/donor through the single needle.

Continuous treatments require two needles, or access points, one for withdrawal of blood and one for return. The withdrawal site is normally an artery although a vein could also be used, and a needle and a pump are used to provide the blood to the therapeutic machine. It is relatively simple to detect a problem with withdrawal, for instance, if the withdrawal needle is dislodged. Bubbles form in the withdrawal line and conventional air sensors detect the bubbles. Detecting a problem in the return of the blood to the patient is more difficult. The return line typically includes a needle with venous access. If the return line is dislodged, the blood is not returned to the patient, but may continue to be pumped and may accumulate near the patient, but not returned to the patient's vascular system. Depending on the pumping rate of the blood and the time for treatment, this could have life-threatening effects on the patient within a very short period time.

Accordingly, a number of apparatuses have been devised for detecting needle dislodgement, especially venous dislodgement. An example is U.S. Pat. Appl. Publ. 2006/0130591. In a device according to this application, a venous needle is equipped with a photosensor and is covered with an opaque patch. This device would not send a signal or an alarm if the needle begins leaking or is only slightly dislodged. The photosensor could also fail to detect light because the needle has not been dislodged sufficiently to expose the photosensor to light.

Another example is U.S. Pat. No. 7,052,480, in which an induction coil is attached to a venous blood line and a second coil is attached to the arterial blood line. An electric current is generated and injected into the blood circuit, passing from one coil through the blood to the second coil. Signal processing circuitry is able to detect any variation in the resulting current in the second coil, and can interpret any significant change in the current, impedance, voltage, resistance, and so forth, as an indication of a leak or of dislodgement. This technique is complicated and difficult to set up for consistent, reliable operation, in consideration of natural variances over long periods of time, and also considering differences between patients.

Another example is provided in U.S. Pat. 7,060,047, in which an electric signal is also injected into the patient and is used to form a capacitor. A ring electrode is placed around the tubing of the venous branch, between the drip chamber of a hemodialysis machine and the access needle returning blood to the patient. The blood of the patient forms the other plate of the capacitor. An electronic circuit is used to monitor the voltage across the plates of the capacitor. When the venous access needle is dislodged, a large change in the voltage results, and is detected by the electronic circuit. This technique has the disadvantage that a voltage change may not result until the blood has been exhausted and no longer fills the tubing in the return line.

Numerous other techniques have been devised, many of them depending on a flow of blood causing conductivity between two electrodes or two wires. One problem with these methods is that it is not easy to distinguish between small amounts of blood and the natural perspiration of a person, which can cause false alarms. What is needed is a better way of quickly detecting dislodgement of a venous or other needle or catheter from a patient, so that inadvertent loss of blood and harm to the patient is avoided.

SUMMARY

One embodiment is an access disconnect detector. The access disconnect detector includes at least one radio-frequency transmitter, at least one radio-frequency receiver, and a mount suitable for mounting the at least one radio-frequency transmitter and at least one radio-frequency receiver, wherein the mount and the at least one transmitter and receiver are configured for positioning adjacent an access site for detecting a presence of blood of a patient, and wherein the access site is positioned between the at least one radio-frequency transmitter and the at least one radio-frequency receiver so that the at least one radio-frequency receiver receives one level of signals from the at least one radio-frequency transmitter when the access site is dry and receives a lower level of signals when the access site is wetted.

Another embodiment is an access disconnect detector. The access disconnect detector includes a flexible mount suitable for attaching to a patient, an array including at least one radio-frequency transmitter and at least one radio-frequency receiver mounted on a first side of the mount, and a pad of absorbent material on the array, wherein the mount and the at least one transmitter and at least one receiver are configured for positioning adjacent a dialysis access site for detecting a presence of blood of the patient, and wherein the at least one transmitter and at least one receiver are configured so that the at least one receiver receives one level of signals from the at least one transmitter when the at least one transmitter and the at least one receiver are dry and receives a lower level of signals when one of the at least one transmitter and at the least one receiver is wetted with blood.

Another embodiment is an access disconnect detector. The access disconnect detector includes at least one radio-frequency transmitter for placement on a person, at least one radio-frequency receiver for placement on a person, and a flexible layer adjacent the at least one transmitter and the at least one receiver, wherein the transmitter and the receiver are mounted on a single side of the flexible layer for rapid detection of blood from the person.

Another embodiment is a method for detecting an access site disconnection. The method includes steps of placing at least one radio-frequency transmitter and at least one radio-frequency receiver adjacent the access site, sending a transmission from the at least one radio-frequency transmitter to the least one radio-frequency receiver, receiving the transmission at a baseline level by the at least one radio-frequency receiver, periodically repeating the steps of sending and receiving, and sending a signal if the transmission sent by the at least one radio-frequency transmitter is not received at the baseline level by the at least one of the radio-frequency receiver.

Additional features and advantages are described herein, and will be apparent from, the following Detailed Description and the figures.

DETAILED DESCRIPTION

Figure 1:
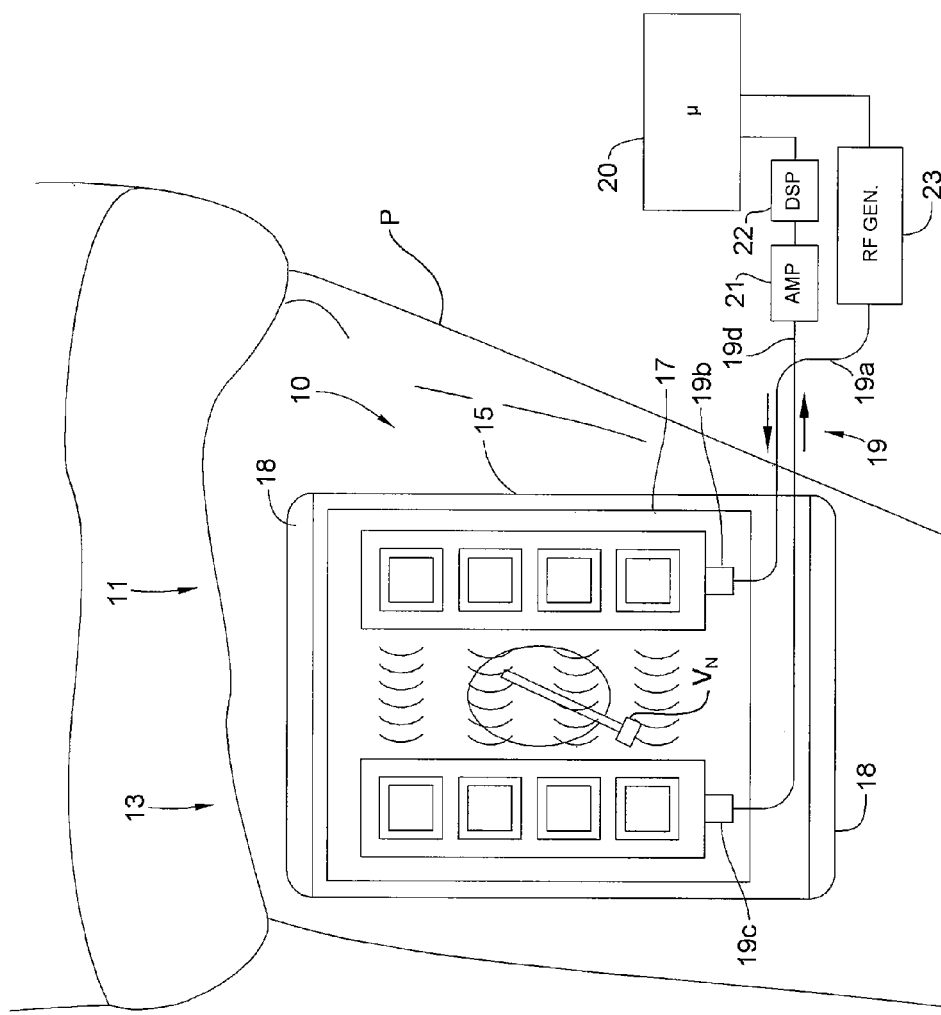
FIG. 1 depicts a plan view of a first embodiment of an access disconnect detector.

There are many embodiments of the invention, of which only a few are described in the figures and detailed description below. A first embodiment of an access disconnect detector is depicted in FIG. 1. Access disconnect detector 10 is mounted on arm A of a patient, near a venous access site V with a venous access needle $V_n$. In this embodiment, the detector includes a first plurality 11 of radio-frequency transmitters and a first plurality 13 of radio-frequency receivers. In this application, the term transmitter refers to either an active or passive transmitting antenna. A passive antenna may be used to reduce the size, complexity, and cost of the detector. The term receiver refers to either an active or passive receiving antenna. A passive antenna may be used to reduce the size, complexity, and cost of the detector. The frequencies of interest are any frequencies generally referred to as radio frequencies, from as low as about 50 kHz to 10 GHz. Other ranges of interest include 2 GHz to 6 GHz, which includes the commonly-used 2.45 GHz and 5.8 GHz. 5.8 GHz in particular uses very small antenna.

The transmitters are mounted on one side of the access site, with the receivers mounted on the opposite side. The pluralities 11, 13 of transmitters and receivers are mounted on one side of a mounting pad 15, with the transmitters and receivers mounted adjacent the patient, rather than on the side of the mounting pad facing away from the patient. There may also be a layer of absorbent material 17 on the other side of the transmitters and receivers, the absorbent material intended for placement on the patient and on the access site using strips of adhesive 18. The detector 10 is connected by cable 19, including coaxial cable 19a, splitter 19b, combiner 19c, and cable 19d, to a controller 20, which may also include a power source for the detector.

The mounting pad is flexible so that its shape is adaptable to the exact shape of the patient's arm or leg, or other access site. Silicone pads may be used, as may urethane pads. Other elastomers may be used, as may other suitable plastic materials. The absorbent material makes the detector more acceptable to the patient by presenting a soft, comfortable surface to the patient. The absorbent material also wicks blood and better enables the detector to retain even small amounts of blood that leak from the access site. The absorbent material wicks blood and moves at least some of the blood by surface tension to the area between the transmitters and receivers.

Figure 11:
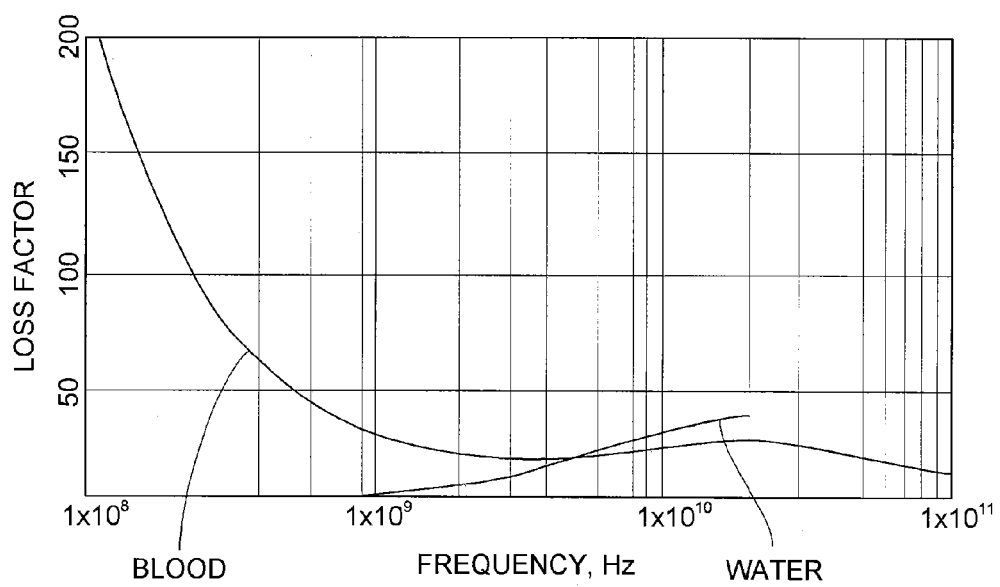
FIG. 11 depicts the effect of frequency on the loss factors of blood and water.

It is well known that liquids tend to scatter radio frequency radiation. Thus, when blood flows into or is wicked into areas between the transmitters and receivers, the radio frequency radiation is scattered and is not received at the receivers, at least not at the signal intensity that was received before the leakage or disconnect from the access site. A large amount of sweat absorbed into the bandage could cause a small change in signal intensity. However, blood has a higher loss factor (the rate at which radio frequency radiation is absorbed) than water, which is the main component of sweat. See FIG. 11. The salt in sweat would also cause a small amount of RF absorption, but the concentration of salt in sweat is much lower than that of blood. Therefore the reduction in signal (from baseline) will be significantly higher with a blood accumulation than if the patient were to sweat. This can be used when setting up and calibrating the system for use with patients.

It will be clear to those having skill in the art that a plurality of radio frequency transmitters and receivers will do an excellent job of detecting blood leakage from an access site from which the access needle has become disconnected. It is not necessary to have a plurality of transmitters and receivers, because a single transmitter and a single receiver, located on opposite sides of the access site are also fully capable of detecting blood. More than one transmitter and more than one receiver may also be used, at the price of a small bit of additional weight and discomfort to the patient. The mounting pad and the detector as a whole may become heavier and larger as more transmitters and receivers are added. While each transmitter and receiver may be very small, some no larger than 1 square cm, the cumulative area they occupy, along with connections and other components, grows with the number of transmitters and receivers added.

Figure 2:
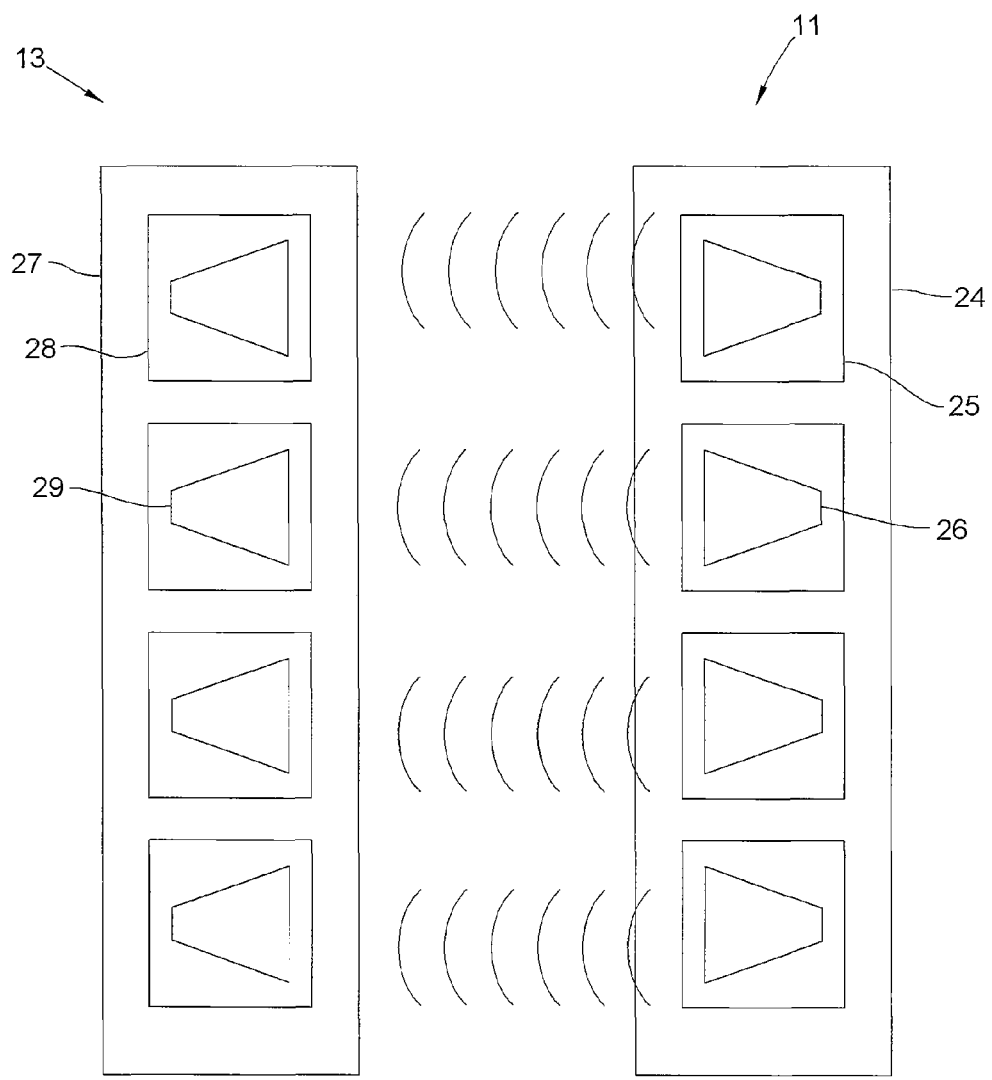
FIG. 2 depicts additional elements of the embodiment of FIG. 1.

The radio transmitters and receivers may be mounted individually or may be mounted on a single circuit as shown in FIGS. 1-2. The transmitter circuit 11 includes a polyimide flex circuit layer 24. An alternate material also well-suited for radio frequency application is Rogers R/Flex. Polyimide may be plated with copper or other suitable conductive material. Ceramic material such as that of Rogers 6010, or other circuit board material, even FR-4, epoxy-fiberglass, or other materials, may also be plated and etched to make suitable antennae. On the top side, a top layer of copper is etched to prepare the four tapered patch antennae 26 shown. The bottom layer of the circuit board also includes a copper layer 25, that has been etched to form a ground plane under each of the antennae.

The receiver circuits are constructed in a virtually identical manner, with a circuit board 27, receiver antennae 29, and a ground plane 28 for each antenna. Using a dual-plane circuit board with antennae as shown, each antenna will transmit radio frequency waves off the forward edge of the antenna, that is, each will be edge-firing. This will direct the radio frequency beams directly as the transmitter antennae are aimed, that is, directly across the access site to the row of receiver circuits. These are examples of microstrip antennae. A microstrip antenna generally includes a dielectric substrate with a ground plane on one side and a conductor on the other side. The conductor and the ground plane are typically made of copper. The conductor is also surrounded by a second dielectric, which may be air or may be another dielectric.

Since these are radio frequency waves, it is necessary to use radio-frequency equipment, e.g., coaxial cable, to transmit the waves from an RF generator to the transmitting antennae 26 and from the receiving antennae 29. Coaxial cables 19a, 19b each have a center conductor and shielding, typically a copper or steel mesh type material. The center conductor is connected to a splitter 19b, which connects to the center conductor and then divides into four additional connectors, one for each antenna 26. On the receive side, each antenna connects to a combiner 19c, which may be the same as the combiner 19b. Combiner 19c connects to the center conductor of coaxial cable 19d. The shielding of cable 19d connects to the ground planes 28 of the receive antennae. RG-178, for example, is a lightweight, flexible, and small diameter (2-3 mm) coaxial cable. SMA (sub-miniature A) type connectors can also be used, and slip-on type SMA connectors can be used for quick connect/disconnect connections.

The radio frequency waves are generated by an RF generator 23, as part of a detector circuit or as part of the therapy machine. The detector circuit also includes an amplifier 21 to receive and amplify the captured signal and signal processing circuitry 22 to process the received data and to determine whether the signal is within a desired range, or whether blood has been detected.

The amount of material and its location on the access site should be controlled, e.g., by adhering the absorbent material in place by sewing to the mounting pad 15, or by carefully using an adhesive, or hook-and-loop fasteners, such as those available under the trademark Velcro®, to adhere the absorbent material to the pad or to the circuit board or flex circuit for the transmitters and receivers. Adhesives may be used, but they may contain small residual amounts of water that may scatter the radio-frequency radiation. A sleeve or pad may also be wrapped around the patient's arm or leg and secured with metallic or plastic fasteners, or with hook-and-loop fasteners.

In one way of using this embodiment, a health care professional or a care giver, or even the patient himself or herself, may administer hemodialysis or other therapy. An arterial access needle (not shown) and the venous access needle are connected to a therapy machine and inserted into the patient. The care giver or patient then places the detector pad over the access site and secures it in place using adhesive strips 18 that are placed on the outer perimeter of the detector 10 or the pad 15, and are not placed between the transmitters and the receivers. The therapy machine is turned on and the controller 20 is activated. Controller 20 may be a stand-alone controller for the detector, or may be part of the therapy machine, such as a hemodialysis machine or apheresis or blood separation machine.

The transmitters and receivers are given an initial reading to determine whether they are working properly. After adjusting for particular on-site parameters, the detector is optimized for acceptable transmit/receiver power and reception levels. This may be considered a base line or initialization level. Once therapy has begun, the transmitters may be programmed to periodically send a radio-frequency signal to the receivers, such as once or twice per second, or even more often, or less often. In one embodiment, a signal is sent from at a rate from about 0.5 Hz (about once every two seconds) to about 2 Hz (or about twice per second). Other rates may be used. The receivers receive the signal at a commensurate power level. If a signal is not sent, there may be something amiss with the transmitter or the control circuitry. If a signal is not received, there may be something amiss with the receiver or the control circuitry, or it may be that blood has been detected. If blood enters the absorbent material, or the area between the transmitters and receivers, the radio frequency radiation is scattered and the signal detected by the receiver will be diminished. The diminishment, or the extent of the diminishment, may be determined by experiment and used to calibrate or "train" the particular detector or hemodialysis setup being used.

Figure 3:
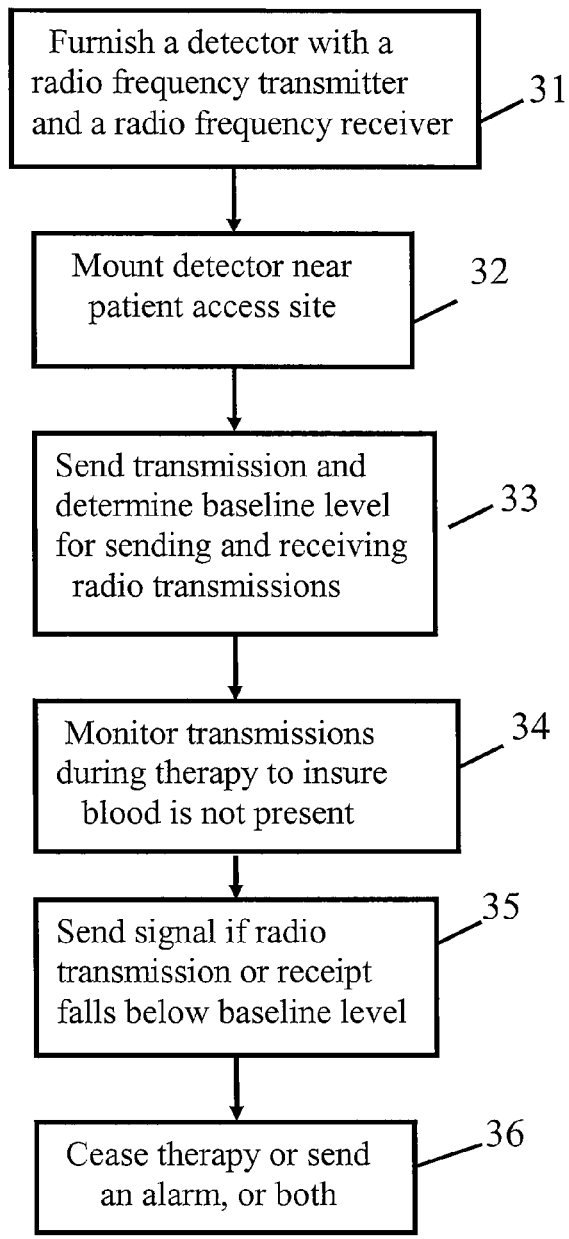
FIG. 3 depicts a flow chart showing a method of using an access disconnect detector.

Several steps of a method of using the radio-frequency blood detector are depicted in the flowchart of FIG. 3. As mentioned, the detector that is furnished 31 is a pad with one or more radio frequency transmitters and receivers. The detector is mounted 32 near the patient access site. The controller is turned on and initialized, and a first radio transmission is made through the transmitters and receivers. A baseline level for transmission power and receipt is determined 33 and the equipment is ready. Therapy is then begun, and as mentioned, periodic transmissions are made 34 through the transmitters and receivers to insure that blood is not present. A short burst of signals may be sent at intervals of about one-tenth of a second to about every second, i.e., 1-10 Hz, or at other intervals, from about 0.5 to about 2 Hz. If the controller notes that the receiver is not receiving power at the baseline level, or that the transmitter is not sending a signal at the baseline level, a signal may be sent 35 to the therapy machine or to a caregiver. As a result, therapy may be ceased 36, or an alarm or an alert sounded, or both.

Figure 4:
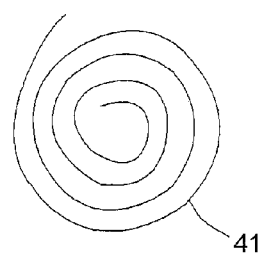
FIGS. 4-9 depict circuits and antennae useful in embodiments of an access disconnect detector.
Figure 5:
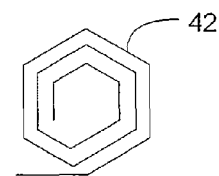
Figure 6:
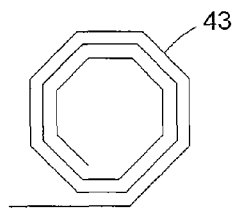

Coaxial cable is needed to contain the RF signal and maintain its integrity. Circle, square, or other polygon patch antennas fire (transmit) the radio wave in a direction that is perpendicular to the broad face of the sensor. Other antennae suitable for face-firing radio antennae include the spiral planar antenna depicted in FIGS. 4-6, a spiral antenna 41, a hexagon 42 and an octagon 43. These antenna are useful in this application for aiming the radio transmissions at an angle to the access site rather than straight across the access site.

Figure 7:
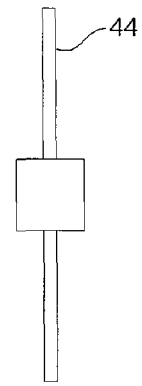
Figure 8:
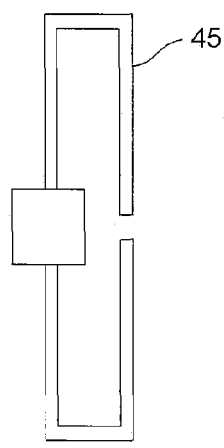
Figure 9:
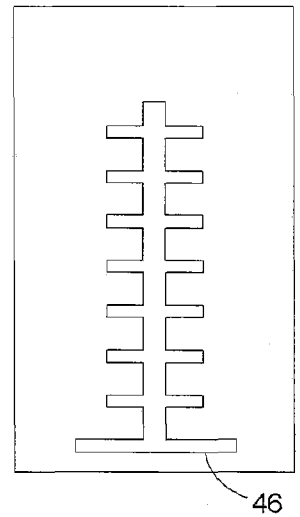

Another type of firing mode is edge-firing. Single and double dipole antennae are depicted, respectively, in FIGS. 7 and 8. These devices include single dipole antennae 44 and dual dipole 45. Another example of an antenna that works well for edge-firing applications is the Yagi-type antenna 46 depicted in FIG. 9. They may be used to send or receive signals. Each of these antennae may be used to transmit as well as to receive. Each is an example of a microstrip antenna and each may be made by the same etching process used for etching printed circuit boards. They may also be made by printing processes, e.g., using ink-jet printing with conductive inks.

Figure 10:
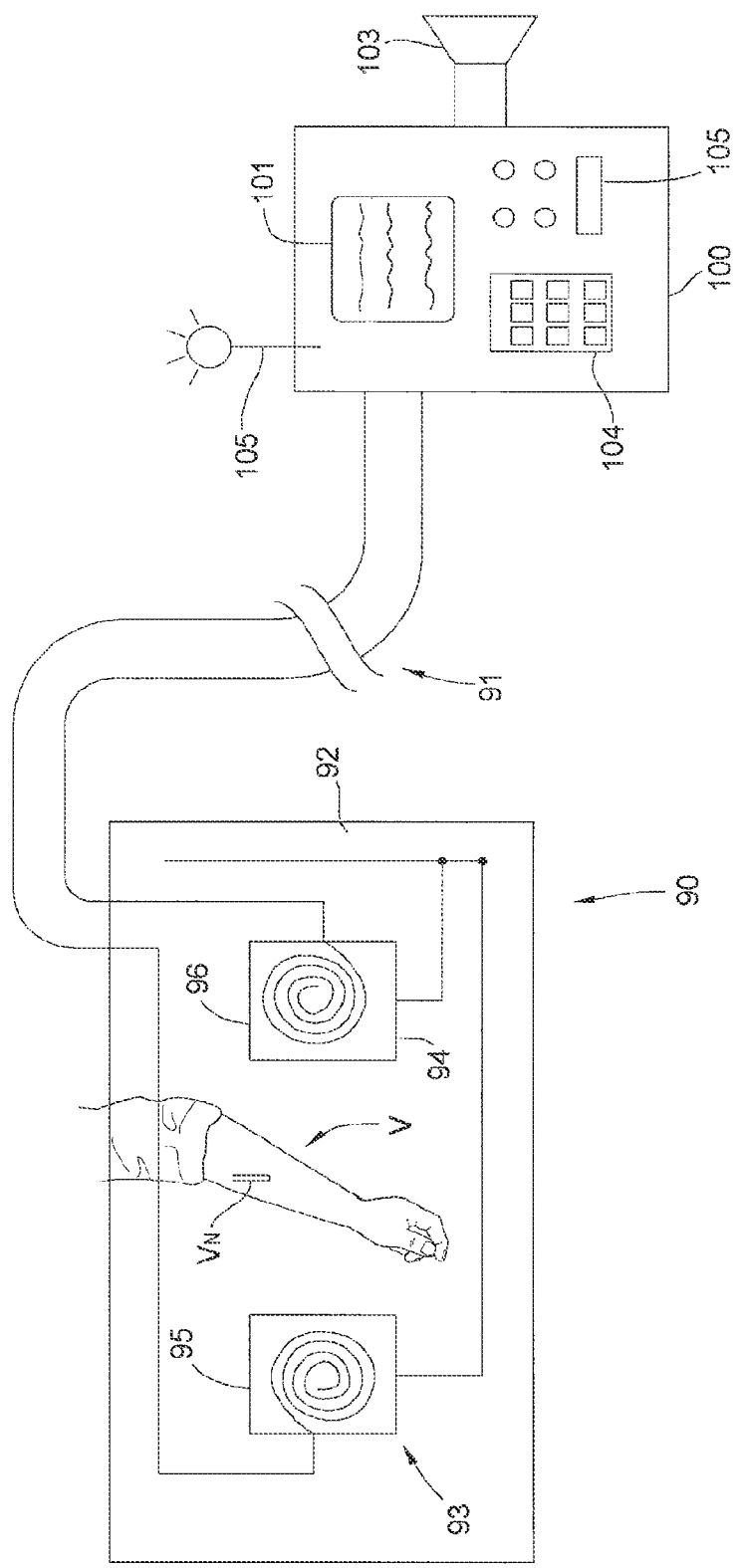
FIG. 10 depicts another embodiment of a radio frequency access disconnect detector.

Another example of an access disconnection detector using radio-frequency transmitters and receivers is depicted in FIG. 10. Detector 90 is connected to a controller or control circuitry 100 via coaxial cables 91. The detector includes a flex circuit 92, with one radio frequency transmitter 93, intended for placement on one side of the venous access site V and access needle $V_n$, and a radio frequency receiver 94, intended for placement on an opposite side of the access site. The transmitter and receiver each have a spiral antenna as shown and a ground plane 95, 96.

Cable 91 is lightweight and extends to controller 100 for carrying the RF signals. Controller 100 may be a stand-alone controller for the access disconnect detector, or it may be a part of a therapy machine, such as a hemodialysis or apheresis machine. Controller 100 includes circuitry and logic necessary to generate radio frequency signals to the transmitter and to receive, process and interpret signals received from the detector and the receiver. The controller includes a microprocessor and at least sufficient logic, in the form of software on a computer readable medium, to interpret the RF transmissions and to send a signal if blood is detected by the blood detector. The signal may be to cease therapy and to alert the patient or the caregiver via local screen 101, local speaker 103, through antenna 105, or via a wired connection,. The controller also includes inputs, such as a keyboard 104 and a disc drive 105 for input/output. There may also be a wired input via standard wire cable or fiber optic, such as for a hospital information system or a clinic computer system.

The logic includes guidelines for the amount of signal reduction that is required before an alert or an alarm is sounded. For example, the detector and the controller may be programmed to require three consecutive signals in which the RF transmission received is only half of the expected level before sending a signal or an alert. Some other signal loss level may be used, and a greater or lesser number of consecutive or non-consecutive signals may be used instead. The idea is to use more than one transmitter-receiver pair to avoid dependence on a single signal for blood detection, and to use more than a single signal to also avoid false alarms, which may unduly delay needed therapy, while also safeguarding the patient from blood loss.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. An access site disconnection detection method comprising:
sending a radio-frequency transmission;
receiving the radio-frequency transmission when the access site is dry to establish a baseline level;
repeating the sending of the radio-frequency transmission at least once;
receiving the at least one repeated radio-frequency transmission at a level that has fallen below the baseline level if the access site is wet; and
sending a blood leakage detection signal in response to the at least one repeated radio-frequency transmission having fallen below the baseline level.

2. The access site disconnection detection method of claim 1, which includes sending the radio frequency transmissions at a frequency of about .5 Hz to about 2 Hz.

3. The access site disconnection detection method of claim 1, which includes sending the radio frequency transmissions at a frequency of about 1 Hz to about 10 Hz.

4. The access site disconnection detection method of claim 1, which includes generating the sent radio-frequency transmissions via a controller of a blood treatment machine.

5. The access disconnection detection method of claim 1, which includes sending the signal in response to the at least one repeated radio-frequency transmission having fallen below the baseline level as sensed by any one of a plurality of radio-frequency receivers.

6. The access site disconnection detection method of claim 1, which includes issuing an alarm and/or stopping a pump in response to the sending of the blood leakage detection signal.

7. The access site disconnection detection method of claim 1, which includes sending the blood leakage detection signal if the at least one repeated radio-frequency transmission falls below half of the baseline level.

8. The access site disconnection detection method of claim 1, which includes mounting at least one radio-frequency transmitter and at least one radio frequency receiver on at least one electrical circuit.

9. The access site disconnection detection method of claim 8, wherein the at least one electrical circuit is flexible.

10. The access site disconnection detection method of claim 1, which includes absorbing blood leaking from an access site disconnection with an absorbent layer.

11. An access site disconnection detection method comprising:
sending a radio-frequency transmission;
receiving the radio-frequency transmission when the access site is dry to establish a baseline level;
repeating the sending of the radio frequency transmission a plurality of times;
receiving the repeated radio-frequency transmission a plurality of times at a level that has fallen below the baseline level if the access site is wet; and
sending a blood leakage detection signal in response to the repeated radio-frequency transmission having fallen below the baseline level a plurality of times.

12. The access site disconnection detection method of claim 11, which includes sending the radio frequency transmissions at a frequency of about .5 Hz to about 2 Hz.

13. The access site disconnection detection method of claim 11, which includes sending the radio-frequency transmissions from a first circuit board to a second circuit board.

14. The access site disconnection detection method of claim 11, which includes sending the radio-frequency transmissions via antennae of at least one radio-frequency transmitter and receiving the radio-frequency transmissions via antennae of at least one radio-frequency receiver.

15. The access site disconnection detection method of claim 14, wherein the antennae is selected from the group consisting of (i) spiral antennae, (ii) single dipole antennae, (ii) double dipole antennae, or (iv) a Yagi-type antennae.

16. The access site disconnection detection method of claim 11, which includes sending the radio-frequency transmissions at an angle relative to the access site.

17. The access site disconnecting detection method of claim 11, which includes receiving the repeated radio-frequency transmission a plurality of times at the baseline level when no blood leakage has occurred at the access site.

18. An access site disconnection detection method comprising:
   setting a baseline level for a radio-frequency transmission received by at least one radio-frequency receiver when the access site is dry;
   sending a radio-frequency transmission from at least one radio-frequency transmitter;
   receiving the radio-frequency transmission by the at least one radio-frequency receiver at a lower level than the baseline level if the access site is wet; and
   sending a blood leakage detection signal in response to the radio-frequency transmission being received at the lower level.

19. The access site disconnection detection method of claim 18, which includes setting the baseline level prior to a blood treatment therapy.

20. The access site disconnection detection method of claim 18, which includes sending the blood leakage detection signal in response to the radio-frequency transmission being received at the lower level a plurality of consecutive times.

\* \* \* \* \*